United States Patent [19]

Davis et al.

[11] Patent Number: 4,788,135

[45] Date of Patent: Nov. 29, 1988

[54] SYSTEM FOR EFFICIENT ISOLATION OF GENES USING PROBES

[75] Inventors: Ronald W. Davis; Richard A. Young, both of Menlo Park, Calif.

[73] Assignee: The Board of Trustees of the Leland Stanford, Jr. University, Stanford, Calif.

[21] Appl. No.: 786,883

[22] Filed: Oct. 10, 1985

Related U.S. Application Data

[63] Continuation of Ser. No. 472,544, Mar. 7, 1983.

[51] Int. Cl.[4] .................... C12Q 1/68; C12N 15/00; C12N 1/00
[52] U.S. Cl. .......................................... 435/6; 935/31; 935/79; 935/80; 435/172.3; 435/320
[58] Field of Search .................... 435/172.3, 68, 317, 435/6; 935/31, 79, 80

[56] References Cited

U.S. PATENT DOCUMENTS 4,466,917 8/1984 Nussenzweig et al. ........... 435/172.3

OTHER PUBLICATIONS

Skalka and Shapiro, *Gene* (1976), 1:65-79.
Sanzey et al., *Proc. Natl. Acad. Sci. USA*, (1976), 73:3394-3397.
Erlich et al., *Cell,* (1978), 13:681-689.
Broome and Gilbert, *Proc. Natl. Acad. Sci. USA*, (1978), 75:2746-2749.
Clarke et al., Methods Enzymol., (1979), 68:436-442.
Kemp and Cowman, *Proc. Natl. Acad. Sci. USA*, (1981), 78:4520-4524.
Leder et al, Science, vol. 196, pp. 175-177, Apr. 1977.
Williams and Blattner, (1980), Bacteriophage Lambda Vectors for DNA Cloning in *Genetic Engineering,* 2:201.

*Primary Examiner*—Alvin E. Tanenholtz
*Attorney, Agent, or Firm*—Bertram I. Rowland

[57] ABSTRACT

Systems are provided for the dual purpose of cloning genes using antibodies as probes and isolating unknown proteins encoded by cloned DNA. The method employs a vector derived from phage which is used in combination with a high frequency lysogenic host. The vector is further characterized by having an inducible promoter regulating expression of a gene into which the foreign DNA may be introduced to produce a fused protein, and controlled induction of the prophage with rapid increase in copy number and high level transcription of foreign DNA. The technique is exemplified with a specific lambda phage construct in conjunction with the $\beta$-galactosidase structural gene lacZ.

2 Claims, No Drawings

SYSTEM FOR EFFICIENT ISOLATION OF GENES USING PROBES

This application is a continuation of application Ser. No. 472,544, filed Mar. 7, 1983, which disclosure is incorporated herein by reference.

BACKGROUND OF THE INVENTION

1. Field of the Invention

There is a continuing effort to provide for the cloning and expression of DNA sequences. A particularly fruitful approach in obtaining DNA associated with expression products of structural genes found in genomic DNA has been the reverse transcription of messenger RNA and the cloning, manipulation and expression of the reverse transcripts of the messenger RNA. Several expression vectors have been used with various antigen screening techniques to identify recombinant DNA containing clones. However, these techniques lack the sensitivity and efficiency necessary to isolate specific recombinant molecules from cDNA libraries containing $10^5$–$10^7$ clones.

Desirable characteristics of a recombinant expression vector for screening cDNA clones include: propagation in a host cell as a single-copy genomic insert to enhance the stability of the insert containing vector and to facilitate repression of foreign genetic information; response to induction with a rapid increase in copy number and high level transcription of the foreign DNA; features providing for minimizing degradation of the foreign DNA expression product; and means for isolating the intact foreign DNA expression product.

2. Brief Description of the Prior Art

Illustrative of the use of expression vectors and various antigen screening techniques to identify recombinant DNA containing clones are articles by Skalka and Shapiro, *Gene* (1976) 1:65–79; Sanzey et al., *PNAS USA* (1976) 73:3394–3397; Erlich et al., *Cell* (1978) 13:681–689; Broome and Gilbert, *PNAS USA* (1978) 75:2746–2749; Clarke et al., *Methods Enzymol.* (1979) 68:436–442; and Kemp and Cowman, *PNAS USA* (1981) 78:4520–4524. Lambda phage are described by Williams and Blattner (1980) Bacteriophage Lambda Vectors for DNA Cloning in *Genetic Engineering* 2:201 (Setlow and Mullander, eds.).

SUMMARY OF THE INVENTION

Techniques and compositions are provided for the rapid and efficient screening of genomic clones for genes expressing a polypeptide product of interest. Expression vectors are provided which allow for insertion of foreign DNA into a gene to produce a fused protein at high efficiency, isolation of the fused protein by means of the portion of the fused polypeptide native to the expression vector and use of the fused protein to produce antibodies specific for the protein of interest. These antibodies may then be used for isolating protein from the host from which the foreign DNA was obtained. Alternatively, where antibodies are available to the protein of interest, the fused protein may be screened with such antibodies, so that the foreign DNA clone producing the polypeptide of interest may be indentified.

DESCRIPTION OF THE SPECIFIC EMBODIMENTS

Techniques and compositions are provided which allow for rapid screening of genomic clones with high sensitivity and efficiency, so as to allow for the efficient isolation of specific recombinant molecules from cDNA libraries containing greater than $10^5$ clones. The method employs a high copy number expression vector which has a combination of desirable properties. While all of the properties are not essential to obtain enhanced ability to screen cDNA genomic clones, the presence of all of the subsequenly described properties will usually provide for the best results. To that effect, the method employs a phage expression vector, which is inducible as to copy number and desirably as to expression, providing for controlled high level transcription of foreign DNA. Translation occurs as a fused polypeptide, where conveniently the N-terminus is a native polypeptide, which provides for means to isolate the fused protein. The expression vector permits high level transcription and translation with only low level lysis of the host.

A bacteriophage vector is employed in combination with a host which allows for high frequency lysogeny. By using this combination, one is assured of high efficiency of insertion of the expression vector into the genomic host, which ensures the efficient utilization of the engineered phage expression vector. A temperate phage which is stably maintained in the lysogenic state is used to transfect a host which is capable of efficient insertion of the phage into its genome. Thus, the cloning of the entire cDNA bank is reasonably assured, where one may detect clones having a complete transcript of the mRNA or transcripts derived from various fragments of an original messenger RNA due to incomplete reverse transcription, which may in turn be used to obtain the complete messenger.

While less desirable, phage retaining lytic capability may be employed, particularly where a sufficient amount of the expression product can be produced prior to lysis. Various phage may be employed as a vector, such as lambda, T phage, P phage, M phage, and φX174, particularly dsDNA, where the phage has been modified to remove lytic capability, while retaining lysogenic, induction and proliferative capability, once inside the host cell. Induction for rapid increase in copy number should be available, conveniently as a temperature sensitive mutation, so that upon change of temperature, particularly raising of temperature, induction and proliferation of the phage can be achieved.

By providing for high frequency lysogeny and inducible proliferation of the phage, one ensures that one can obtain high level growth of the host while maintaining only a single copy of the phage in the host. Once the host cells have been grown to high density, the excision of the phage may be induced by a temperature change resulting in rapid increase in copy number of the phage. Thus, greatly enhanced yields of the transcription and translational products of the phage may be obtained, simplifying isolation of the fused protein and greatly enhancing the probability of isolating substantial amounts of the fused protein free of the major amounts of other proteins present.

The expression vector will have a transcriptional regulatory system, desirably one which is inducible, so that one can provide for the induced production of the fused protein during the rapid growth of the phage. During the growth of the host cells to high density, there are two major advantages in maintaining a single copy, lysis is avoided; and the metabolic system of the host is not diverted to the production of the fused protein, as well as other protein encoded by the phage.

The regulated gene present in the expression vector may be a complete or incomplete structural gene, preferably at least a substantially complete structural gene, which allows for selection between phage into which foreign DNA has been introduced and in which the foreign DNA is absent. Thus, the expression of the functioning gene is indicative of the absence of the foreign DNA. This may be illustrated by the gene encoding for β-galactosidase, lacZ, whereby employing an auxotrophic host, the ability to hydrolyze galactose-dye indicators, e.g. Xgal, with production of colored clones will be indicative of the absence of the foreign DNA. By further providing for controlled expression of the native gene, one can further enhance the production of the fused protein at the appropriate time, by inducing expression of the fused protein. Induction of expression can be achieved by employing a temperature-sensitive promoter, which responds in a parallel way to the induction of the phage. Therefore, the temperature shift would provide for high copy number of the phage concomitant with the induced expression of the fused protein.

The gene present in the expression vector will conveniently have a unique restriction site at least about 25 bases, preferably at least about 50 bases or more, from the initiation codon. The minimum number of bases will be determined by the need to have a polypeptide of sufficient length so that the fused protein may be isolated by employing antibodies specific for the gene present in the expression vector. Generally, at least eight amino acids are required, preferably at least 12, more preferably at least 20, which corresponds to 24, 36 and 60 bases for coding for such polypeptide. Conveniently, one may have the appropriate restriction site toward the terminal end of the gene, generally at least about 30 bases from the terminus of the structural gene, to ensure that the resulting fused protein is not capable of functioning as the normal expression product and that the product is a fused protein having at least one, preferably a plurality of determinant sites common to the fused protein and the normal product.

In addition, the phage expression vector should be defective in lytic capability. Thus, by employing an appropriate mutant or a phage in which the lytic capability gene has in part or in whole been deleted, one can prevent lysis to any significant degree. Some lysis can be tolerated and, in fact, may occur, which may be due to the effect of the presence of a large amount of the expression vector and its transcriptional and translational products in the host cell.

The host which is chosen will be one which demonstrates a high frequency of lysogeny. Therefore, the host will be a bacterium which is receptive to the insertion of the phage expression vector in the genome and stable maintenance of the foreign DNA insert containing phage expression vector during host multiplication. In addition, it is desirable that the host be defective in protein degradation, being a lon mutant in lacking the genetic capability for effective protein degradation. In this manner, one can further enhance the amount of fused protein available for isolation.

Desirably, the fused protein should be at least about 0.1 weight percent of the total protein of the cells, preferably at least about 0.2 weight percent, more preferably at least about 0.5 weight percent. The greater the amount of the fused protein in relation to the total protein, the easier its isolation and purification.

Conveniently, the clones of interest may be determined by plating on an appropriate filter, replica plated, the cells on one of the plates lysed, and the protein residue screened for the presence of the fused protein with antibodies specific for the protein expression product of the expression vector. By having this expression product allow for selection between the presence and absence of foreign DNA, one can readily distinguish colonies where the fused protein is obtained as distinct from the normal expression product.

The fused protein may then be used for production of antibodies specific for the expression product of the foreign DNA. These antibodies may then be used for the isolation and characterization of the protein produced by the foreign DNA. Alternatively, where the desired protein is known and has been characterized, antibodies specific for the expression product of the foreign DNA may be used for screening for the fused protein. Detection of the fused protein having the appropriate determinant sites will then identify the DNA sequence coding for the foreign protein. The sequence may then be excised, modified as appropriate, and then used for insertion into an expression vector for expression of the desired foreign protein.

Various bacterial hosts can be used, which bacterial hosts have the appropriate functions and properties or such functions and properties may be conveniently introduced into such hosts. Various bacterial hosts include Escherichia, Salmonella, Bacillus, Proteus, etc. For the most part, E. coli will be employed since it is well characterized, strains are available which have the appropriate functions or into which the appropriate functions can be readily introduced, and the cells can be rapidly grown to high density.

Once the host cells have been grown to stationary phase, they will be infected with the foreign DNA containing phage expression vector. Generally, the multiplicity of infection will be relatively low, usually below about two, and conveniently at about one. The infected cells may then be grown in an appropriate nutrient medium to a relatively high density, when they may be spread onto an appropriate filter or plate and the cells incubated to produce individual colonies, followed by replica plating.

One of the plates may be incubated in the presence of nutrient medium for growth to relatively high density, followed by induction of the phage to high copy number and transcription and translation of the fused protein. The cells may then be lysed under conditions where the protein is affixed to the support at the site of the cells from which the protein is derived. Desirably, the DNA is removed by convenient washing with an appropriate buffer containing a DNase. The filter may then be screened with appropriately labeled antibodies, which are radioactive, enzyme or fluorescent labeled antibodies or the complex between antibody and antigen may be screened by employing a labeled protein, such as rheumatoid factor or S. aureus Protein A. The presence of the fused protein may then be detected.

The lysogens can then be isolated from the other plate, incubated to high cell density, induced and lysed to provide for the expression vector having the desired foreign DNA. The foreign DNA may then be excised and used for hybridization to the genome of the host from which the foreign DNA was obtained, for hybridization to mRNA of the host for manipulation and introduction into an expression vector for production of the desired protein, or for screening of mutant foreign DNA sequences.

The following examples are offered by way of illustration and not by way of limitation.

EXPERIMENTAL MATERIALS AND METHODS

Bacterial Strains

Strains are listed in Table 1, infra. BNN98 results from the spontanous loss of the F' episome in BNN94. BNN100, BNN101, BNN102 and BNN103 were constructed by P1 transduction of the relevant alleles (hflA150 from BNN92, supF from BNN99) into BNN93, BNN96 or BNN98. The medium used was Luria Broth, pH 7.5, unless otherwise specified. All media and strain construction were as described by Miller, supra. λ phage were from the collection of the inventors and are described by Williams and Blattner, supra.

Construction of λgt11 (lac5 nin5 cI857 S100)

λgt11 is a derivative of λgt7-lac5 (b522 nin5) and λgt4 (cI857 S100 nin5). To construct this phage, λgt7-lac5 and λ540 (ΔB imm21 nin5) were cleaved with HindIII endonuclease (this and all other restriction enzymes were obtained from New England Biolabs, Inc. and were used in accordance with the directions of the supplier) and the restriction fragments were pooled and then ligated with T4 DNA ligase. The desired phage recombinant produced turbid (imm21), blue (lac5) plaques when the DNA was transfected into E. coli BNN933 and cells were plated on medium containing the chromogenic indicator Xgal. The λgt7-lac5/λ540 hybrid was then crossed with λgt4(cI857 S100 nin5) and recombinants, grown at 42°, were scored for the formation of clear (cI857), blue plaques on Xgal plates. The presence of the amber mutation S100 was confirmed by examining relative plating efficiency on hosts which contained or lacked the amber suppressor supF (BNN45 or BNN93, respectively). Finally, the lac5 cI857 S100 phage were mapped for EcoRI restriction endonuclease cleavage sites. λgt11 contained a single EcoRI cleavage site and was mapped in detail with other enzymes.

Preparation of Antibodies

Rabbit antisera were made against the pancreatic α-amylase of C57 BL/6J mice and against chick ovalbumin. IgG was purified from the sera as described by Broome and Gilbert, supra and stored at a concentration of 5-10 mg/ml.

Examining Lysogens for Antigen Production Using Antibody Probes

BNN91 or BNN103 is grown to stationary phase in Luria Broth pH 7.5 plus 0.1% maltose. Up to $5 \times 10^6$ cells per plate are infected at an m.o.i. of 1.0 for 30' at 32° in 0.1 ml of 10 mM tris, pH 7.5, 10 mM MgSO$_4$. The infected cells are diluted with 0.5 ml of Luria Broth and poured carefully on a Schliecher and Schuell BA85 82 mm nitrocellulose filter which had been placed previously on an LB plate. The liquid culture is spread carefully over the filter and permitted to soak through the filter into the plate (relatively dry plates are useful here). The plate is incubated at 32° for 8 hours, and a replica is made in the following manner. The master filter is removed from its plate and excess liquid is blotted from its underside. Another filter is wetted on an LB plate, blotted, placed over the master, pressed evenly against it and marked with a needle. Both master and replica filters are then replated and incubated at 32°. After one hour, one of the two plates is removed to 42° for 2 hours, the other plate is refrigerated. The induced cells are then lysed on the filter by inverting the plate over a small vessel of chloroform for 15 min. to create a chloroform-saturated atmosphere. The nitrocellulose filter is removed from the plate and submerged in 3 ml buffer A (0.17M NaCl, 0.01M tris HCl pH 7.5) plus 0.01% SDS for 1 hour (this and all subsequent steps are performed at 24°). The solution often becomes viscous at this stage and DNA, if not removed, appears to reduce antigen availability. Therefore, the filter is rinsed in 3 ml buffer A, incubated in 3 ml buffer A plus 2μg/ml DNaseI for 10 min. and then rinsed once again in buffer A. To reduce nonspecific protein binding to the nitrocellulose, filters are incubated in 3 ml buffer A plus 3% BSA for 1 hour. IgG is generally diluted to 50 μg/ml in buffer B (buffer B=buffer A plus 0.1% SDS, 0.1% Triton X100 and 1 mM EDTA) and the filter is gently agitated in this solution for 3 hours. After washing the filter twice in buffer B (10 min. per wash), the bound antibody is allowed to react with approximately $5 \times 10^6$ cpm of $^{125}$I-labeled ($1-2 \times 10^6$ cpm/μg) Protein A (Staphlococcus aureus) in 3 ml buffer B for 1 hour. Finally, the filter is washed 5 times in 5 ml buffer B, 15 min. per wash. Good autoradiographic signals are usually obtained overnight in a screen of $10^6$ colonies/filter.

Preparation of Lysates from Induced Recombinant Lysogens

Lysogens were grown at 30° to a cell density of , induced at 42° for 15 min., then well aerated by shaking at 38° for 2 hours. (Induced lysogens containing some recombinants will lysed after 2 hours at 38°, presumably because of the detrimental effects of the high levels of some hybrid proteins.) Cells were pelleted and quickly resuspended in gel sample buffer (50 mM tris, pH 6.8, 1.5% SDS, 50 mM DTT and 4M urea) at 3% the original volume and mixed well by passaging several times through at 21 gauge needle. The solution was then heated to 70° for 2 min. and insoluble material was removed by centrifugation for 3 min. in a microfuge.

TABLE 1

| Strain | Alias | Genotype |
|---|---|---|
| BNN45 | LE392 | hsdR$^-$hsdM$^+$ supE44 supF thi met lacY |
| BNN91 | MA150 | Δ(pro-lac) hflA150 galK strA |
| BNN92 | MA156 | MA150[chr::Tn10] |
| BNN93 | C600 | hsdR$^-$hsdM$^+$ supE thr leu thi lacY1 tonA21 |
| BNN94 | CSH41 | F' lacI lacP proA$^+$ proB$^+$/Δ(pro-lac) galE thi |
| BNN95 | AB1899 | thr-1 leuB6 thi-1 argE3 his-4 proA2 lon-1 lacY1 glaK2 mtl-1 xyl-5 ara-14 strA31 tsx-33 supE44 |
| BNN96 | SG1041 | Δ(lacIPOZYA)U169 proA$^+$ Δlon araD139 strA thi |
| BNN97 | Y1004 | BNN93(λgt11) |
| BNN98 | Y1048 | F$^-$ Δ(pro-lac) galE thi-1 supF58 |
| BNN99 | Y1059 | F$^+$ supE57 supF58 mel-1 [trpC22::Tn10](λ) |
| BNN100 | Y1068 | F$^-$ Δ(pro-lac) galE thi-1 supF58 |
| BNN101 | Y1070 | F$^-$ Δ(pro-lac) galE thi-1 supF58 hflA150 [chr::Tn10] |
| BNN102 | Y1073 | BNN93 hflA150 [chr::Tn10] |
| BNN103 | Y1083 | BNN96 hflA150 [chr::Tn10] |

TABLE 2

| Name | cDNA | Fragment | Orientation | Frame | Hybrid Length |
|---|---|---|---|---|---|
| αP2 | amyl | 1.5 kb EcoRI | reversed | — | — |
| αP3 | amyl | 1.5 kb EcoRI | proper | in | 142,000 |
| T81 | oval | 2.0 kb TaqI | proper | — | 153,000 |
| T83 | oval | 2.0 kb TaqI | reversed | — | — |
| T104 | oval | 2.0 kb TaqI | proper | out | — |
| P82 | oval | 3.2 kb PvuII | proper | in | 140,000 |

RESULTS

The expression vector λgt11 (lac5 nin5 cI857 S100) was constructed as described in Materials and Methods. The site used for insertion of foreign DNA is a unique EcoRI endonuclease cleavage site located within lacZ, 53 base pairs upstream of the β-galactosidase termination codon. Phage containing inserts generate an inactive β-galactosidase fusion protein; these phage can be distinguished from non-recombinant phage by their inability to produce blue plaques on a lacZ⁻ host on Xgal plates. The vector can accommodate up to 8.3 kb of insert DNA, assuming a maximum packageable phage DNA length of 52 kb. λgt11 cDNA libraries containing $10^5$–$10^7$ recombinant phage (in which recombinants account for 4–30% of total phage) have been constructed using polyadenylated RNA isolated from *S. cerevisiae* strain X2180, *C. elegans* strain CB1490, rat preputial gland and human placenta.

The ability to form lysogens from the λcI857 S100 expression vector can be exploited to maximize the yield of protein synthesized from transcripts of the foreign DNA. The phage vector produces a temperature sensitive repressor and contains an amber mutation which renders it lysis defective (Neubauer and Calef, *J. Mol. Biol.* (1970) 51:1–13; Goldberg and Howe, *Virology* (1969) 38:200–202); consequently lysogens can be induced by temperature shift to accumulate large quantities of phage products in the absence of lysis. To obtain efficient lysogeny, cell strains containing the mutation hflA150 (Belfort and Wulff, *Virology* (1973) 55:183–192) have been used. Essentially every hflA mutant cell is lysogenized when infected with λ, yet cI857 prophage induction remains unhindered. Moreover, hflA affects neither the relative plating efficiency nor the plaque size of λgt11 or λgt11 phage containing recombinant DNA in the otherwise isogenic pair BNN100 and BNN101. Thus, hflA strains can be lysogenized efficiently with λgt11 recombinant DNA libraries and these lysogens can be induced to produce normal phage yields.

Construction of Model Recombinants

To test the ability of λgt11 to express foreign DNA as a fusion product and as a detectable antigen, model recombinants were constructed by inserting mouse α-amylase and chick ovalbumin cDNAs into the EcoRI site of the vector. Since the DNA sequence surrounding the lacZ EcoRI site and the amino acid sequence of β-galactosidase are known, the foreign DNA insertion could be engineered to obtain a continuous (or noncontinuous) coding frame from β-galactosidase into α-amylase or ovalbumin. The origin of the DNA used in these recombinants and the portion of eukaryotic protein they encode are given in Table 2, supra.

Detection of Eukaryotic Antigens

The relative level of antigen detection with induced lysogens containing λgt11 recombinant phage whose inserts vary in orientation and fusion frame was investigated. Purified IgG was used to detect antigen produced by $2 \times 10^6$ lysogenized cells in 4 mm dots on nitrocellulose filters as described in Materials and Methods. Films were exposed for 5–8 hours with a Cronex Lightening Plus intensifying screen at −70°. Good signals were obtained with both α-amylase and ovalbumin 1 gG. All lysogens containing inserts in the proper transcriptional orientation (αP3, T81, T104 and P82) produce detectable antigen; in contrast, αP2 and T83, whose DNA inserts are in the opposite orientation, yield signals comparable to those in control spots. T104, an out-of-frame ovalbumin cDNA insert, produced approximately ⅛ the signal obtained with the lysogen containing the fused polypeptide, T81. This experiment indicates that antigenic detection is dependent upon proper orientation of the insert DNA with respect to the β-galactosidase transcription unit and that the relative signal strength is greatest when the reading frames of lacZ and insert DNA coincide.

Screening λgt11 Recombinant DNA Libraries with Antibody Probes

The following reconstruction experiment illustrates the screening procedure. Approximately 25 MA150 cells lysogenized with a recombinant DNA phage (either a-amylase or ovalbumin) were added to $10^5$, $10^6$ or $5 \times 10^6$ λgt11 lysogens of MA150. Each culture was plated immediately on 82 mm nitrocellulose filters, grown for 8 hours at 32°, replica plated, induced and probed with antisera as described in Materials and Methods. Film exposure was 15 hours with an intensifying screen. Antigen produced by cells containing recombinant phage was detected even at the highest cell density tested ($5 \times 10^6$). However, replica filters retained fewer signals with greater cell density: approximately 5%, 10% and 60% of the signals obtained from the master filter were lost at respective cell densities of $10^5$, $10^6$ and $5 \times 10^6$ per plate. Thus, satisfactory signal reproducibility, at least for the antigen-antibody interaction examined here, is obtained at a plating density of $10^6$ cells/filter.

Production of Fusion Polypeptides

The amount of hybrid protein which accumulates in BNN91 cells containing the λgt11 recombinants αP3, T81 and P82 were determined by subjecting lysates of these lysogens, prepared as described in Materials and Methods, to SDS polyacrylamide gel electrophoresis. Bands exhibiting the mobility predicted for the hybrid proteins were observed when stained with silver (Merrill et al., *PNAS U.S.A.* (1979) 76:4335–4339), but not with the less sensitive Comassie Brilliant Blue, suggesting that very small amounts of the novel proteins accumulate. To improve the yield of these proteins the recombinant phage were lysogenized in the lonΔ mutant strain, BNN103. Since BNN103 increases the stability of β-galactosidase peptide fragments, its lysogens might be expected to accumulate larger quantities of the unstable β-galactosidase hybrids. SDS polyacrylamide gels were employed for comparing the proteins accumulating in induced lon⁺ and lon lysogens containing αP3, T81 and P82. Lysates were prepared as described in Materials and Methods and 20 μl of each were loaded on 7.5% running, 4% stacking polyacrylamide gels, subjected to electrophoresis, and stained with Comassie Brilliant Blue Lysates from lon⁺ and lon lysogens of αP3 were subjected to electrophoresis of greater duration in a repeat run. Lysates from BNN91 and BNN103 and also from BNN91 and BNN103 and also from BNN91/λgt11 and BNN103/λgt11 appear identical. Indeed, the gel showed that BNN103 lysogen lysates contain proteins of the predicted size for both α-amylase (α3) and ovalbumin (P82) hybrids. The T81 fusion protein, with a predicted molecular weight of 153,000, could not be resolved from the RNA polymerase subunit β. Similar results were obtained with another lon mutant, BNN95.

To determine whether the enhanced yield of the full-length fusion polypeptide in lon mutants increases the level of detectable antigen, 4 mm dots of BNN91 and BNN103 lysogens of αP3 ($4 \times 10^5$ cells/dot) were probed as before. The BNN103 lonΔ lysogen was shown to generate about 3-fold greater signal than did the BNN91 lysogen. Thus, BNN103 is useful for enhancing signal-to-noise ratios in high cell density screening of lysogen libraries.

The phage expression vectors of this invention, as exemplified by λgt11, facilitate the identification and isolation of proteins which are specified by previously cloned DNA. The hybrid protein produced by the cells containing the recombinant DNA can be purified and used to obtain antibodies. Antibodies thus produced will include activity against the foreign portion of the protein fusion; these antibodies can then be used as tools to isolate the native protein from the organism host source. The hybrid proteins accumulate in lon mutant strains in amounts amenable to purification. For example, approximately $10^{-15}$ of hybrid protein was obtained which is about 0.5% of the total protein, based on an estimated comparison with known amounts of β-galactosidase on SDS polyacrylamide gels. Thus, 1 mg of hybrid protein could be obtained from cells or about 2 liters of induced culture. The hybrid proteins can be isolated by employing affinity chromatography or purified directly by preparative polyacrylamide electrophoresis.

Thus, the subject invention provides for an efficient simple way for characterizing and screening cDNA genomic clones and isolating the expression products of the cDNA or the genomic DNA of the cDNA host source.

Although the foregoing invention has been described in some detail by way of illustration and example for purposes of clarity of understanding, it will be obvious that certain changes and modifications may be practiced within the scope of the appended claims.

What is claimed is:

1. λgt11.

2. A method for screening a genomic cDNA library which comprises:
   inserting foreign cDNA sequences into λgt11 phage vectors at a unique site in the β-galactosidase gene of said λgt11 wherein expression results in production of fused polypeptides;
   transforming a high-frequency lysogenic bacterial host with said vectors containing said cDNA sequences;
   growing said host to high density and inducing said phage to high copy number with concomitant expression of said fused polypeptides; and
   isolating a fused expression product of said β-galactosidase gene and cDNA.

* * * * *

UNITED STATES PATENT AND TRADEMARK OFFICE
CERTIFICATE OF CORRECTION

PATENT NO. : 4,788,135
DATED : November 29, 1988
INVENTOR(S) : Davis, et al.

It is certified that error appears in the above-indentified patent and that said Letters Patent is hereby corrected as shown below:

Column 1, after the title, please insert the following:

This invention was made with U.S. Government support under contracts GM07818 & GM21891 awarded by the National Institutes of Health and NP-286B awarded by the American Cancer Society. The Government has certain rights in this invention.--

Signed and Sealed this

Eighteenth Day of April, 1995

Attest:

BRUCE LEHMAN

Attesting Officer

Commissioner of Patents and Trademarks